United States Patent
Dorogi et al.

[11] Patent Number: 5,882,661
[45] Date of Patent: Mar. 16, 1999

[54] COMPOSITION AND METHOD FOR TOPICAL APPLICATION TO SKIN, HAIR AND NAILS

[75] Inventors: Peter Ladislavs Dorogi, Norwalk; John Patrick McCook, Guilford; Alan Joel Meyers, Trumbull; Anthony Vargas, Monroe, all of Conn.

[73] Assignee: Elizabeth Arden Co., Division of Conopco, Inc., New York, N.Y.

[21] Appl. No.: 815,822

[22] Filed: Mar. 12, 1997

[51] Int. Cl.$^6$ ................................. A61K 9/48; A61K 7/00
[52] U.S. Cl. ................. 424/401; 514/847; 424/70.1; 424/61
[58] Field of Search .................... 424/401, 70.1, 424/61; 514/847

[56] References Cited

FOREIGN PATENT DOCUMENTS

| 0 720 847 | 1/1995 | European Pat. Off. . |
| 95/29151 | 11/1995 | WIPO . |
| 96/16635 | 6/1996 | WIPO . |

OTHER PUBLICATIONS

Ceramides Brochure, "Human Skin–identical Ceramides", 1984, by H. Lambers et al., pp. 2–8.

*Primary Examiner*—Sally Gardner-Lane
*Attorney, Agent, or Firm*—Milton L. Honig

[57] ABSTRACT

A composition and method thereof treating or conditioning human skin, hair or nails is described. The composition is topically applied in an effective amount and contains from about 0.0001 to about 50 wt. % of a ceramide derivative containing sphingoid bases having amide, but not ester linkages to a 2 (alpha)-hydroxy carboxylic acid and a safe and effective amount of a pharmaceutical or cosmetically acceptable carrier. The composition effectively treats or conditions areas of fine flakes having histogram values of 10 to 128. Treated areas exhibit a desquamation value difference of 1.0 or greater at day 28 after treatment commences compared to a desquamation value of untreated areas.

3 Claims, No Drawings

COMPOSITION AND METHOD FOR TOPICAL APPLICATION TO SKIN, HAIR AND NAILS

FIELD OF THE INVENTION

The present invention pertains to a composition and method for a topical application to human skin, hair and nails for the treatment and conditioning of fine flake areas. The compositions contain selected ceramides which have an alpha hydroxy group and no ester linkages.

THE RELATED ART

The top layer of human skin or the epidermis is composed of many different cell types, including keratinocytes, melanocytes and langerhans cells. Keratinocytes are the major cell type of the epidermis totalling about 75% of the cells in the human epidermis. Within the epidermis the keratinocytes reside in four different stages of differentiation. The basal layer rests on the basal lamina separating epidermis from the dermis. These cells are large columnar rapidly proliferating cells. These basal cells migrate upward within the epidermis, initiated by the process of differentiation.

The layer above the basal cells is the spinous layer. Cells in the spinous layer initiate the production of proteins characteristic of the differentiated epidermis. Lying above the spinous layer is the granular layer which is characterized by electron dense granules. It is the granular layer which is responsible for the synthesis of lipid molecules required for the formation of the water impermeable barrier of the skin. Finally the top most layer of the skin is the stratum corneum which is formed from the granular layer by the destruction of cellular organelles.

The corneocytes are embedded in a bed of specific lipid structures and this structure provides the protective barrier for the skin. The outer most layer of corneocytes is peeled off from the skin during the normal process of desquamation. Differentiation of the epidermal keratinocytes is the driving force for the normal desquamation process to occur. Epidermal differentiation is important for providing the essential function of the skin, namely to provide a protective barrier against the outside environment and to prevent loss of water from the body. The most differentiated cells of the stratum corneum do not have the ability to grow.

Clinically desquamation is measured as either fine flakes or coarse flakes for the purpose of evaluating product efficiency. The methodology conventionally used relies upon histogram values as described in Miller, D. L., *Skin Pharmacology*, 5:227 (1992).

The present invention is based, in part, on the discovery that selected ceramides significantly reduce the occurrence of fine flakes in skin which in turn results in increased benefits to the skin such as improved conditioning, moisturizing and treatment of photodamaged skin and various skin disorders.

Cosmetic compositions are known which utilize ceramides (lipids found in skins) and pseudo ceramides (synthetic molecules resembling ceramides) to control water loss and/or to repair damage (eg. dry, flaky, chapped, wrinkled) skin by replacing the skins natural lipids. See, for example, U.S. Pat. Nos. 5,476,661 (Pillai et al.); 5,206,020 (Critchley et al.); 5,198,210 (Critchley et al.); 5,175,321 (Ohashi et al.); 4,985,547 (Yano et al.); and 4,778,823 (Kawamata et al.). The art has taught that ceramides alone do not induce keratinocytes differentiation, except at higher levels. Keratinocyte differentiation is required to provide the normal desquamation process which provides smooth, conditioned and moisturized skin. Because of the cost of ceramides, there is an incentive to keep the level of the compounds in the formulation at a minimum.

It has thus been discovered that commercially feasible levels of selected ceramides provide maximum reduction in fine flakes of desquamation to provide improved overall skin appearance. It is thus an object of the invention to provide compositions for treating the skin while avoiding the disadvantages of the art.

It is another object of the invention to provide a skin treatment composition which contains selected ceramides to prevent the formation of fine flakes in treated skin.

It is yet another object of the invention to provide a method for treating or preventing the appearance of fine flakes in skin to provide improved overall skin appearance.

These and other objects of the invention have become more apparent from the detailed description and examples which follow.

SUMMARY OF THE INVENTION

The above objects are obtained by the present invention which includes, in part, a composition containing:
  (i) from about 0.0001% to about 50 wt. % of a ceramide material having an alpha hydroxide and no ester linkages; and
  (ii) a safe and effective amount of a pharmaceutically or cosmetically acceptable carrier.

The preferred ceramides include Ceramide IV, Ceramide V and Ceramide VI, preferably Ceramide VI.

The present invention also includes a method of improving or preventing the appearance of flaky, wrinkled, aged, photodamaged skin and treating skin disorders. The method includes topically applying to the skin a composition containing the selected ceramide compounds.

The compositions of the invention are intended for topical application to dry skin which contains fine, flaky skin.

DETAILED DESCRIPTION OF THE INVENTION

The inventive compositions contain as a first essential ingredient ceramide derivatives having a number two (alpha)-hydroxy carboxylic acids linked via an amide linkage to a sphingoid base. Examples of such compounds include:

1. 2-hydoxyethanoic acid (glycolic acid)
2. 2-hydroxypropanoic acid (lactic acid)
3. 2-methyl 2-hydroxypropanoic acid (methyllactic acid)
4. 2-hydorxybutanoic acid
5. 2-hyroxypontanoic acid
6. 2-hydroxyhexanoic acid
7. 2-hydroxyheptanoic acid
8. 2-hydroxyoctanoic acid (alpha-hydroxycaprylic acid)
9. 2-hydroxynonanoic acid
10. 2-hydroxydecanoic acid
11. 2-hydroxyundecanoic acid
12. 2-hydroxydodecanoic acid
13. 2-hydroxytetradecanoic acid (alpha-hydroxylauric acid)

The three classes of ceramide which are essential in the invention, Ceramide IV, Ceramide V and Ceramide VI are naturally present in the mammalian skin and range from 16 to 30 carbon atoms; species below 16 carbon atoms are not found in nature and are not part of the present invention.

Besides the ceramides, the compositions of the present invention will utilize a cosmetically acceptable carrier. The carrier may either be aqueous, anhydrous or an emulsion. Preferably the compositions are aqueous, especially water and oil emulsions of the W/O or O/W variety. Water when present will be in amounts which may range from 5 to 95%, preferably from 20 to 70%, optimally between 35 and 60% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 25 to 40% by weight.

Emollient materials may also serve as cosmetically acceptable carriers. These may be in the form of silicone oils and synthetic esters. Amounts of the emollients may range anywhere from 0.1 to 50%, preferably between 1 and 45% by weight, optimally between 10 and 40 wt. %.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C.

Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono- and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters and squalane are satisfactory polyhydric alcohol esters. Also useful are $C_{11}$–$C_{30}$ non-ring ester derivatives of salicylic acid such as tridecyl salicylate.

(4) Wax esters such as beeswax, spermaceti, myristyl myristate, stearyl stearate.

(5) Sterols esters, of which cholesterol fatty acid esters are examples thereof.

The most preferred esters are $C_{11}$–$C_{30}$ non-ring ester derivatives of salicylic acid such as tridecylsalicylate.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably butylene glycol. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982®), hydrophobically-modified acrylates (e.g. Carbopol 1382®), polyacrylamides, cellulosic derivatives and natural gums. Among useful cellulosic derivatives are sodium carboxymethylcellulose, hydroxypropyl methylcellulose, polyacrylamide hydroxypropyl cellulose, hydroxyethyl cellulose, ethyl cellulose and hydroxymethyl cellulose. Natural gums suitable for the present invention include guar, xanthan, sclerotium, carrageenum, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

Cosmetic compositions of the present invention may be in any form. These forms may include lotions, creams, roll-on formulations, mousses, aerosol and non-aerosol sprays and pad-applied formulations.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, $C_8$–$C_{20}$ alkyl ether phosphates and combinations thereof.

Sunscreen actives may also be included in compositions of the present invention. Particularly preferred are such materials as ethylhexyl p-methoxycinnamate, available as Parsol MCX, and benzophenone-3, also known as Oxybenzone. Inorganic sunscreen actives may be employed such as microfine titanium dioxide. Amounts of the sunscreen agents will generally range from 0.1 to 30%, preferably from 2 to 20%, optimally from 4 to 10% by weight.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition.

Compositions of the present invention may also contain water-soluble vitamins. The term water-soluble defines substances with a solubility of at least 0.1%, preferably at least 1%, optimally at least 5% by weight in water. Illustrative water-soluble vitamins are Niacin, Vitamin $B_2$, Vitamin $B_6$, Vitamin C and Biotin. One source for Vitamin C is a product sold under the trademark of Vitazyme available from the Brooks Company. Niacin, Vitamin B and Biotin are available from Roche Pharmaceuticals. Total amount of vitamins in compositions according to the present invention may range from 0.001 to 1%, preferably from 0.01 to 0.6, optimally from 0.1 to 0.5% by weight.

Keratolytic agents such as $C_2$–$C_{25}$ a-hydroxy alkanoic acids may also be incorporated into compositions of this invention. Illustrative of this group of materials are glycolic, lactic, α-hydroxyoctanoic acids, esters and salts thereof. The salts may be selected from alkalimetal, ammonium and $C_1$–$C_{20}$ alkyl or alkanolammonium counterions. Levels of α-hydroxyalkanoic acids may range from 0.001 to 10%, preferably between 0.2 and 1%, optimally between 0.4 and 0.5% by weight. A beta hydroxy alkanoic acid which may be used includes salicylic acid.

Another adjunct ingredient can be that of an enzyme. Particularly preferred is superoxide dismutase, commercially available as Biocell SOD from the Brooks Company, USA.

Natural vegetable materials from renewable resources are often desirable in cosmetic compositions. For instance, cosmetic compositions of the present invention may include β-glucan derived from oats.

Colorants, fragrances, opacifiers and abrasives may also be included in compositions of the present invention. Each of these substances may range from about 0.05 to about 5%, preferably between 0.1 and 3% by weight.

USE OF THE COMPOSITIONS

The compositions according to the invention is attended primarily as a product for topical application to human skin to reduce fine flakes in order to reduce moisture loss and enhance the flexibility and quality of skin. The composition can also be applied to hair and nails.

In use, a small quantity of the composition, for example from 1 to 5 ml, is applied to exposed areas of the skin, from a suitable container or applicator and if necessary it is then spread over and/or rubbed into the skin using the hand or fingers or a suitable device.

Product Form and Packaging

The topical skin and/or hair treatment composition of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finer operation. When the composition is a cream, it can simply be stored in a non-deformable bottle or squeeze container,such as a tube or a lidded jar. the invention accordingly also provides a closed container containing a cosmetically acceptable composition as herein defined.

The composition may also be included in capsules such as those described in U.S. Pat. No. 5,063,507, incorporated by reference herein.

The following Examples will more fully illustrate embodiments of this invention. All parts, percentages and proportions referred to herein and in the appended claims are by weight unless otherwise indicated.

EXAMPLE 1

Fine flake areas and subsequent desquamation values were determined using Bioscan OPTIMAS v4.1, Microsoft EXCEL v7.0, StatSoft STATISTICAL "Flood Lamps" appropriately positioned for even lighting and the methodology described in Miller, D. L., Presentation at the 9th ASBS Symposium, Sendai, Japan, 1992 described in *Skin Pharmacology* 5:227 (1992).

For purposes of this invention the fine flake areas of the invention exhibit histogram values of from level 10 to level 128. Specifically, the image capture system was set to "flat" response i.e. the contrast and brightness were adjusted to 50% of their variable range. The camera lens aperture was adjusted to give a mean gray level of 130 units when the target was a standard brightness reference surface. Under the selected magnification, the D-SQUAME® disc fills the entire monitor screen and a typical disc with scales on its exhibits both black background in areas not covered by scales and bright areas where there are dense flakes.

The gray level histogram of the captured image was obtained by the Bioscan software program, 4 reported parameters were derived from the histogram which reports the sample area percentage observed at each of 256 levels of brightness as follows:

1. Average brightness of the sample under standardized lighting conditions; ranges from 0 to 225 increasing with the overall amount and thickness of dry skin scales.[1]

[1] Recorded but not used in statistical analysis.

2. Percent (times 10) of the sample area covered by fine flakes. This is the sum of the histogram values from level 10 to level 128 representing the thinnest flakes.

3. Percent (times 10) of the sample area covered by coarse flakes. This is the sum of the histogram from level 129 to 244 representing the highly reflective thick flakes.

4. The desquamation index (Shatz et al.) derived from the formula:

n=1 to 5

$D_i = (2A + \Sigma[T_n = (n-1)])/5$

A = Percent area covered by all scales $T_n$ = Sum of percent of scale area in histogram range assigned to thickness level n n = Thickness level ranging from 1 to 5 (5 equal sized ranges of the histogram).

EXAMPLE 2

The following illustrates the significant effectiveness of Ceramide VI (within the scope of the invention) compared to Ceramide III (outside the scope of the invention) on treating the defined fine flake areas.

A base formulation was prepared having the following formula:

| Ingredient | % Active |
|---|---|
| Deionized water | 43.4 |
| Amigel | 0.1 |
| Glycerin | 3.0 |
| Deionized Water | 19.6 |
| Carbopol 1382 | 0.4 |
| Carbopol 1382 | 0.4 |
| Na2EDTA | 0.1 |
| Methylparaben | 0.15 |
| Silicone 200 (10 CST) | 0.4 |
| Linoleic Acid | 0.1 |
| Cetiol LC | 4.4 |
| Syncrowax AW1-C | 2.5 |
| Spectron SA-13 | 0.0 |
| Bernel Ester TOC | 3.0 |
| BRIJ 721 (VEG) | 1.2 |
| BRIJ 72 (VEG) | 0.3 |
| Waxenol 822 | 1.5 |
| Emulgade 1000 NI | 1.7 |
| Shea butter | 1.5 |
| Propylparaben | 0.1 |
| A-C 400 Polyethylene | 0.4 |
| Xalfin 15 | 1.0 |
| PMMA | 1.0 |
| Water | 2.0 |
| Tea 99% | 1.4 |
| Dow Corning 344 | 6.0 |
| Tocopherol | 0.1 |
| Actiglide Special | 1.0 |
| Seamollient | 0.5 |
| Water | 2.0 |
| Vitazyme C | 0.0 |
| DL-Panthenol | 0.5 |
| Glydant | 0.3 |
| Colorants & Fragrances | 0.3 |

Samples were prepared containing the base formula alone, 5 wt % Ceramide III, plus the base and 5 wt % Ceramide VI plus the base. Selected panelists were evaluated for dryness of the stratum corneum using D-squame® adhesive disks supplied by CuDerm Company. The D-squame® samples were taken from the lower leg between the ankle and the knee for both legs of each panelist.

The fine flake areas were determined as described in Example 1.

The panelists underwent a four week treatment phase during which time one leg was treated twice daily with a test sample while the other leg remained as an untreated control. Desquamation value for the test sites were determined as described in Example 1 with the following results.

| Day | Base Untreated | Base Treated | Ceramide III plus Base Untreated | Ceramide III plus Base Treated | Ceramide VI plus Base Untreated | Ceramide VI plus Base Treated |
|---|---|---|---|---|---|---|
| 0 | 2.8 | 2.8 | 2.8 | 2.7 | 3.1 | 3.0 |
| 1 | 3.1 | 3.2 | 3.3 | 3.2 | 3.3 | 3.0 |
| 3 | 3.1 | 3.0 | 3.4 | 2.9 | 3.0 | 2.9 |
| 7 | 3.1 | 2.9 | 3.6 | 3.2 | 3.0 | 2.3 |
| 15 | 2.9 | 2.6 | 3.3 | 2.3 | 3.2 | 1.6 |
| 21 | 3.7 | 2.6 | 3.9 | 2.3 | 3.2 | 1.6 |
| 28 | 3.4 | 2.4 | 3.1 | 2.4 | 3.0 | 1.3 |

As observed above, there was a significant reduction in the presence of fine flake areas beginning about day 7 and forward after treatment commenced for skin areas treated with the composition of the invention versus untreated areas. The reduction in fine flake area continued unabated for the remainder of the test period. At day 28 it was observed that the desquamation value for the treated areas was different from the desquamation value for the untreated areas by a value of 1.7.

In contrast fine flake areas treated with Ceramide III containing compositions, which are outside the scope of the invention, did not show a marked improvement untreated areas until day 15. Additionally from day 15 forward the desquamation values for the treated areas plateaued at around 2.3 and exhibited a difference in desquamation values of the untreated areas of only 0.7 at day 28.

Clearly, compositions and methods of using the compositions with the invention ore effective in treating or conditioning flakes than those outside of the invention.

EXAMPLE 3

A skin creme formulation according to the present invention is described in the table below:

| Ingredient | % Active |
|---|---|
| Deionized water | 43.4 |
| Amigel | 0.1 |
| Glycerin | 3.0 |
| Deionized Water | 19.6 |
| Carbopol 1382 | 0.4 |
| Carbopol 1382 | 0.4 |
| Na2EDTA | 0.1 |
| Methylparaben | 0.15 |
| Silicone 200 (10 CST) | 0.4 |
| Linoleic Acid | 0.1 |
| Cetiol LC | 4.4 |
| Syncrowax AW1-C | 2.5 |
| Spectron SA-13 | 0.0 |
| Bernel Ester TOC | 3.0 |
| BRIJ 721 (VEG) | 1.2 |
| BRIJ 72 (VEG) | 0.3 |
| Waxenol 822 | 1.5 |
| Emulgade 1000 NI | 1.7 |
| Shea butter | 1.5 |
| Propylparaben | 0.1 |
| A-C 400 Polyethylene | 0.4 |
| Xalfin 15 | 1.0 |
| PMMA | 1.0 |
| Water | 2.0 |
| Tea 99% | 1.4 |
| Dow Corning 344 | 6.0 |

-continued

| Ingredient | % Active |
|---|---|
| Tocopherol | 0.1 |
| Actiglide Special | 1.0 |
| Seamollient | 0.5 |
| Water | 2.0 |
| Vitazyme C | 0.0 |
| DL-Panthenol | 0.5 |
| Glydant | 0.3 |
| Colorants & Fragrances | 0.3 |
| Ceramide VI | 5.0 |

We claim:

1. A method for preventing formation of fine flakes in skin comprising treating the skin with a composition comprising from about 0.0001 to about 50 wt. % of Ceramide VI delivered in a safe and effective amount of a pharmaceutically or cosmetically acceptable carrier.

2. The method according to claim 1 wherein the composition further comprises water-soluble vitamins.

3. The method according to claim 1 wherein the cosmetically acceptable carrier is an aqueous carrier.

* * * * *